United States Patent
Maass, Jr. et al.

(10) Patent No.: US 7,425,664 B2
(45) Date of Patent: Sep. 16, 2008

(54) DENTAL ABSORBENT PAD

(76) Inventors: Thomas H. Maass, Jr., 1450 Ridgeway Dr., Acworth, GA (US) 30102; Perry L. Parke, 121 N. Lakeside Dr., Kennesaw, GA (US) 30144

( * ) Notice: Subject to any disclaimer, the term of this patent is extended or adjusted under 35 U.S.C. 154(b) by 197 days.

(21) Appl. No.: 11/025,429

(22) Filed: Dec. 29, 2004

(65) Prior Publication Data
US 2006/0142718 A1    Jun. 29, 2006

(51) Int. Cl.
*A61F 13/15* (2006.01)
*A61F 13/20* (2006.01)
*A61C 5/00* (2006.01)

(52) U.S. Cl. .................. 604/358; 433/140; 604/378

(58) Field of Classification Search .............. 604/358, 604/370, 388, 387, 373; 433/140, 168.1, 433/229
See application file for complete search history.

(56) References Cited

U.S. PATENT DOCUMENTS

| | | | |
|---|---|---|---|
| 3,888,248 A * | 6/1975 | Moore et al. ............ 602/43 |
| 3,989,867 A * | 11/1976 | Sisson ................. 428/132 |
| 4,605,402 A * | 8/1986 | Iskra ................... 604/368 |
| 4,813,944 A * | 3/1989 | Haney et al. ............ 604/358 |
| 4,925,453 A * | 5/1990 | Kannankeril ........... 604/378 |
| 4,938,819 A * | 7/1990 | Ishii et al. ............. 156/78 |
| 5,169,575 A * | 12/1992 | Koenhen et al. ........ 264/41 |
| 5,891,121 A * | 4/1999 | Redwine et al. ........ 604/387 |
| H2062 H * | 4/2003 | Blaney et al. .......... 602/46 |
| 2005/0137562 A1* | 6/2005 | Mizutani et al. ...... 604/385.17 |

* cited by examiner

*Primary Examiner*—T. Zalukaeva
*Assistant Examiner*—Melanie J. Hand
(74) *Attorney, Agent, or Firm*—Baker Donelson et al.

(57) ABSTRACT

A dental absorbent pad (10) is disclosed having a moisture permeable, outer layer (11), a moisture absorbent layer (12), a stiffening plate (13), and a moisture impermeable backing (14). The moisture absorbent layer and stiffening plate are smaller in size than the overlying outer layer and backing so that a margin (17) is formed thereby which surrounds the moisture absorbent layer and stiffening plate. The margin is very flexible and therefor comfortable to a patient undergoing a dental procedure.

9 Claims, 1 Drawing Sheet

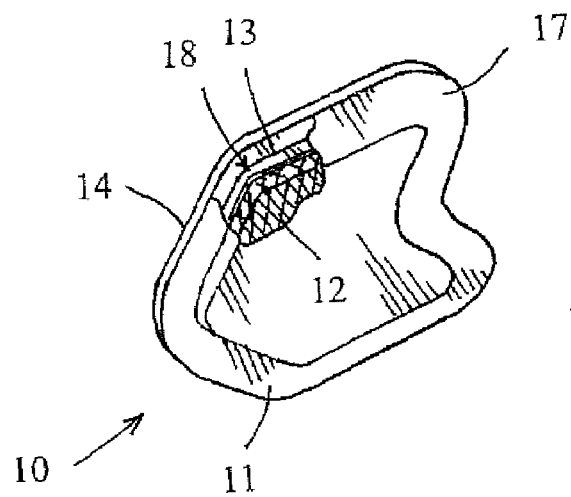
Fig. 1
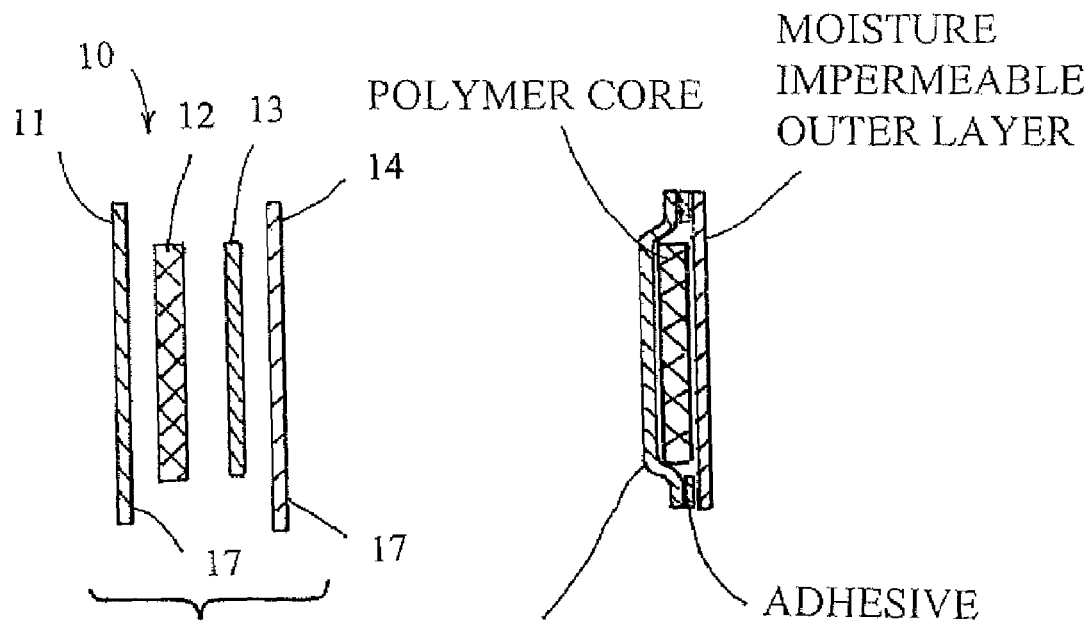
Fig. 2
Fig. 3
PRIOR ART

DENTAL ABSORBENT PAD

TECHNICAL FIELD

This invention relates generally to absorbent pads, and particularly absorbent pads which are used in the dental industry.

BACKGROUND OF THE INVENTION

Small absorbent pads or points are often used in dentistry to absorb saliva from the mouth of a patient during a dental procedure. These pads are typically positioned between the teeth and cheek or between the teeth and tongue and are replaced when they become saturated.

Today, the most effective dental absorbent pads typically have a moisture permeable outer layer made of a nylon fabric, a super absorbent polymer core, and a moisture impermeable, second outer layer of polyethylene film, as shown in FIG. 3. These materials are held together with a thick layer of hardened, hot-melt adhesive. This hardened adhesive however causes the peripheral edges of the pad to be stiff and abrasive, which may cause irritation to the tissue of the mouth.

Accordingly, it is seen that a need remains for a dental absorbent pad which is more comfortable for a patient. It is to the provision of such that the present invention is primarily directed.

SUMMARY OF THE INVENTION

In a preferred form of the invention a dental absorbent pad comprises a moisture permeable outer layer, a moisture absorbent layer positioned adjacent the moisture permeable outer layer, a stiffening plate positioned adjacent the moisture absorbent layer opposite the moisture permeable outer layer, and a backing layer positioned adjacent the stiffening plate opposite the moisture absorbent layer. The stiffening plate has a size and shape smaller than the size and shape of the moisture permeable outer layer and the backing layer to create a peripheral margin portion upon the moisture permeable outer layer and backing layer. The peripheral margin portion of the moisture permeable outer layer is bonded to the peripheral margin portion of the backing layer.

BRIEF DESCRIPTION OF THE DRAWING

FIG. 1 is a perspective view of a dental absorbent pad in a preferred form of the invention.

FIG. 2 is a cross-sectional view of the dental absorbent pad of FIG. 1.

FIG. 3 is a cross-sectional view of a prior art dental absorbent pad.

DETAILED DESCRIPTION

With reference next to the drawings, there is shown in FIGS. 1 and 2 a dental absorbent pad 10 embodying principles of the invention in a preferred form. The pad 10 has a moisture permeable, outer or front layer 11, a moisture absorbent layer 12, a stiffening plate or layer 13, and a moisture impermeable backing or back layer 14. The moisture absorbent layer 12 and stiffening plate 13 are smaller in size than the overlying outer layer 11 and backing 14 so that an approximately 0.5 cm margin 17 is formed by the outer layer 11 and backing 14 extending beyond and around the absorbent layer 12 and plate 13, i.e., the outer layer 11 and backing 14 are adhered to each other along their periphery to form a thin, flexible margin 17. An internal cavity 18 is formed within the peripheral margin and between the outer layer 11 and backing 14. As such, the combination of the outer layer 11 and backing 14 form an outer covering while the combination of the absorbent layer 12 and plate 13 form a core.

The moisture permeable outer layer 11 may be made of a micro-thin high density polyethylene woven or non-woven netting, such as the 0.11 mm non-woven film model number DELNET P530 HDPE sold by Delstar Technologies, Inc. of Middletown, Del. The absorbent layer 12 may be made of composite composed of high performance cellulose fibers and granular super absorbent polymer, such as the 0.76 mm material sold as model number Chem-Posite 11C-130 by Emerging Technologies, Inc. of Greensboro, N.C. The stiffening plate 13 may be made of a 6 mil polystyrene film such as that sold as model number Opticite 500 by Interfilm Corporation of Piedmont, S.C. The backing 14 may be made of a 2.3 mil white cavitated (BOPP) polypropylene film, such as that sold by Palmetto Custom Films International of Piedmont, S.C.

To construct the pad 10 the stiffening plate 13 is treated with a very thin layer of medical grade, rubber based pressure sensitve adhesive, such as model number DM-1187 sold by DermaMed of Tallmadge, Ohio. The stiffening plate 13 is pressed against the absorbent layer 12 to form a bond therebetween. Also, the backing 14 is treated with an extremely thin layer of pressure sensitive adhesive, such as model number DM-1187 sold by DermaMed of Tallmadge, Ohio. The backing is pressed against the stiffening plate 13 and the peripheral portion of the moisture permeable, outer layer 11 to form a bond therebetween to form the peripheral margin 17.

It should be understood that as the margin 17 area of the pad is formed from very thin and flexible layers of material and adhesive, this area of the pad is not considered to be stiff, as opposed to prior art pads. Furthermore, the reduction in stiffness and thickness of this peripheral area reduces the abrasiveness of the peripheral edge against the mouth tissues, thereby further increasing the comfort of the present invention over prior art dental absorbent pads.

It should be understood that the composition of the material is not intended to be limited by those recited herein and may be different from that specifically used in the preferred embodiment. For example, the outer layer 11 may be made of a thin woven, non-woven or porous material, such as a polymer material, woven nylon or non-woven fiber. Similarly, the absorbent layer 12 may be made of other types of conventionally known absorbent material, such as an acrylate polymer. The stiffening plate 13 may be made of any non-reactive material, such as that made of nylon, polyester, polyethylene or fiberboard.

It thus is seen that a dental absorbent pad is now provided which is more comfortable for a patient. And though the invention has been shown and described in its preferred form, it should be understood that additions, deletions and modifications may be made without departure from the spirit and scope of the invention as set forth in the following claims.

The invention claimed is:

1. A dental absorbent pad comprising:
    a moisture permeable outer layer;
    a moisture absorbent layer positioned adjacent said moisture permeable outer layer;
    a moisture impermeable stiffening plate positioned adjacent said moisture absorbent layer opposite said moisture permeable outer layer; and
    a backing layer positioned adjacent said stiffening plate opposite said moisture absorbent layer;

said stiffening plate having a size and shape smaller than the size and shape of said moisture permeable outer layer and said backing layer to create a peripheral margin portion upon said moisture permeable outer layer and said backing layer; and said peripheral margin portion of said moisture permeable outer layer being bonded to said peripheral margin portion of said backing layer.

2. The dental absorbent pad of claim 1 wherein said moisture absorbent layer and said stiffening plate have the same shape and size.

3. The dental absorbent pad of claim 2 wherein said moisture absorbent layer is adhered to said stiffening plate.

4. The dental absorbent pad of claim 1 wherein said moisture permeable outer layer is a polyethylene outer layer.

5. The dental absorbent pad of claim 4 wherein said polyethylene outer layer is a netting.

6. A dental absorbent pad comprising a flexible outer covering having a moisture permeable front layer and a back layer bonded to said front layer along a peripheral margin, said peripheral margin defining an internal cavity between said front layer and said back layer, and a core positioned within said cavity, said core having a moisture absorbent layer and a moisture impermeable stiffening layer, whereby the stiffening layer provides rigidity to a middle portion of the pad while the peripheral margin remains flexible.

7. The dental absorbent pad of claim 6 wherein said moisture absorbent layer is adhered to said stiffening layer.

8. The dental absorbent pad of claim 6 wherein said front layer is a polyethylene outer layer.

9. The dental absorbent pad of claim 8 wherein said polyethylene front layer is a netting.

* * * * *